United States Patent
Strober et al.

(10) Patent No.: US 6,479,465 B2
(45) Date of Patent: Nov. 12, 2002

(54) METHODS OF TREATING COLITIS USING STAT-4 ANTI-SENSE OLIGONUCLEOTIDES

(75) Inventors: Warren Strober, Bethesda, MD (US); Ivan Fuss, Bethesda, MD (US); Markus Neurath, Mainz (DE); Atsushi Kitani, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/812,028

(22) Filed: Mar. 19, 2001

(65) Prior Publication Data

US 2002/0077308 A1 Jun. 20, 2002

Related U.S. Application Data

(63) Continuation of application No. 09/535,025, filed on Mar. 24, 2000, now abandoned
(60) Provisional application No. 60/125,877, filed on Mar. 24, 1999.

(51) Int. Cl.[7] .................. C07H 21/04; C07H 21/02; A61K 48/00; C12Q 1/68; C12N 15/86
(52) U.S. Cl. .................. 514/44; 435/6; 435/91.1; 435/91.3; 435/325; 435/375; 536/23.1; 536/23.2; 536/24.3; 536/24.31; 536/24.33; 536/24.5
(58) Field of Search .................. 435/6, 91.1, 91.3, 435/325, 375; 536/23.1, 23.2, 24.3, 24.31, 24.33, 24.5; 514/44

(56) References Cited

U.S. PATENT DOCUMENTS 5,639,858 A 6/1997 Hoey et al.
5,756,700 A 5/1998 Hoey et al.

OTHER PUBLICATIONS

Simpson et al. "T Cell–mediated Pathology in Two Models of Experimental Colitis Depends Predominantly on the Interleukin 12/Signal Transducer and Activator of Transcription (Stat)—4 Pathway, but Is Not Conditional on Interferon γ Expression by T Cells." *J Exp Med* 187(8): 1225–1234, Apr. 20, 1998.

Neurath et al. "Local administration of antisense phosphorothioate oligonucleotides to the p65 subunit of NF–κB abrogates established experimental colitis in mice." *Nature Medicine* 2(9): 998–1004, Sep. 1996.

Neurath et al., "Antibodies to Interleukin 12 Abrogate Established Experimental Colitis in Mice." *J Exp Med* 182:1281–1290, Nov. 1995.

Jacobson et al., "Interleukin 12 Signaling in T Helper Type 1 (Th1) Cells Involves Tyrosine Phosphorylation of Signal Tranducer and Activator of Transcription (Stat)3 and Stat4." *J Exp Med* 181:1755–1762, May 1995.

Anderson, W. French "Human gene therapy" *Nature* 392: 25–30, Apr. 1998.

Branch, Andrea D. "A good antisense molecule is hard to find" *TIBS* 23; 45–50, Feb. 1998.

Verma and Somia "Gene therapy–promises, problems and prospects" *Nature* 389:239–242.

Agrawal, Sudhir "Antisense oligonucleotides: towards clinical trials" *TIBTech* 14: 376–387, Oct. 1996.

*Primary Examiner*—Andrew Wang
*Assistant Examiner*—Karen Lacourciere
(74) *Attorney, Agent, or Firm*—Needle & Rosenberg, P.C.

(57) ABSTRACT

The present invention provides a method of treating or preventing the inflammatory response of an inflammatory bowel disease in a subject, comprising administering to the subject an amount of a STAT-4 antisense oligonucleotide effective in treating or preventing the inflammatory response of the inflammatory bowel disease.

10 Claims, 2 Drawing Sheets

METHODS OF TREATING COLITIS USING STAT-4 ANTI-SENSE OLIGONUCLEOTIDES

This application is a continuation of U.S. Pat. No. 09/535,025 filed Mar. 24, 2000, now abandoned, which claims priority from provisional patent application Serial No. 60/125,877, filed Mar. 24, 1999, which is hereby incorporated in its entirety by this reference.

BACKGROUND OF THE INVENTION

1. Field of the Invention

The present invention relates to a method of preventing or treating the inflammatory response of an inflammatory bowel disease by administering anti-sense oligonucleotides of the signal transducer and activator of transcription-4 (STAT-4).

2. Background Art

There is growing evidence that Crohn's disease (CD) and ulcerative colitis (UC), the two major forms of human inflammatory bowel disease (IBD) are due to dysregulated intestinal immune responses to one or more luminal antigens in the normal intestinal microflora (1–4). These responses are characterized by abnormalities of both CD4+ and CD8+ T cells which manifest both as disordered T cell activation and regulatory function and as cytokine production disturbances that lead to inflammation (2, 5–9).

Over the last several years, various murine models of chronic intestinal inflammation resembling IBD have been established which have provided important new insights into the pathogenesis of both CD and UC (10). Thus, in studies of several of the models most closely resembling CD it has been shown that production of large amounts of Th1-type cytokines, e.g., interferon-γ (IFN-γ) and tumor necrosis factor-α (TNF-α), by CD4+ T cells is a major and essential feature of the inflammation (6–7, 11). In addition, it has been demonstrated that this disease-causing Th1 cytokine response can be counteracted by induction of a suppressor response involving the generation of T cells producing Th2-type cytokines (IL-4, IL-10) and/or suppressive cytokines, such as TGF-β (12–16). Finally, it has been shown that the Th1 cytokine production in these models is triggered by increased production of IL-12, a cytokine that plays a major role in driving T cell differentiation (17). In the latter regard, increased IL-12 production can be detected in the inflamed intestinal tissues of mice with experimental inflammation and, more importantly, systemic administration of anti-IL-12 to such mice leads to abrogation of the inflammation (7, 11). The relevance of these findings to CD is inherent in studies showing that this disease is also associated with an excessive Th1 T cell response characterized by increased IFN-γ production by lamina propria (LP) T cells (9). In addition, a recent report indicates that CD LP cells produce small, but measurable increases, in IL-12 in response to LPS (18).

Interleukin-12 (IL-12) is a structurally unique cytokine with several important effects on immune function (17, 19–20). It consists of two disulfide-linked subunits, p40 and p35, which form functionally active p40/p35 heterodimers or, alternatively, inactive p40 homodimers which inhibit the activity of the heterodimers in some systems (17). IL-12 is produced mainly by macrophages/monocytes and to a lesser extent by B cells and follicular dendritic cells. It mediates its biological effects by binding to a receptor comprised of a $\beta_1$ chain and a $\beta_2$ chain which are differentially expressed in Th1 and Th2 T cells (21–25): while the $\beta_1$ chain is expressed in both cell types, the $\beta_2$ chain is expressed only in Th1 cells. Thus, it is the expression of the $\beta_2$ chain that accounts for the responsiveness of Th1 cells and the non-responsiveness of Th2 cells to IL-12 (24–25). After IL-12 binds to its receptor, it induces activation of specific members of the STAT (Signal Transducers and Activators of Transcription) family of transcription factors (STAT-3 and STAT-4), which then translocate to the nucleus and bind to genomic promoter regions, including that governing IFN-γ (26–28). STAT-4 is particularly important in this respect, as shown by the fact that STAT-4-deficient T cells manifest impaired production of IFN-γ upon stimulation with antigen (29). In addition, the phenotype of the IL-12-deficient mouse (30) is similar, if not identical, to that of the STAT-4-deficient mouse (29).

The present invention provides STAT-4 anti-sense oligonucleotides which are effective in the treatment and prevention of the inflammatory response of an IBD.

SUMMARY OF THE INVENTION

The present invention provides a method of treating or preventing the inflammatory response of an inflammatory bowel disease in a subject, comprising administering to the subject an amount of a STAT-4 antisense oligonucleotide effective in treating or preventing the inflammatory response of the inflammatory bowel disease.

The present invention may be understood more readily by reference to the following detailed description of specific embodiments and the Examples included herein.

DESCRIPTION OF THE PREFERRED EMBODIMENTS

Figure 1:
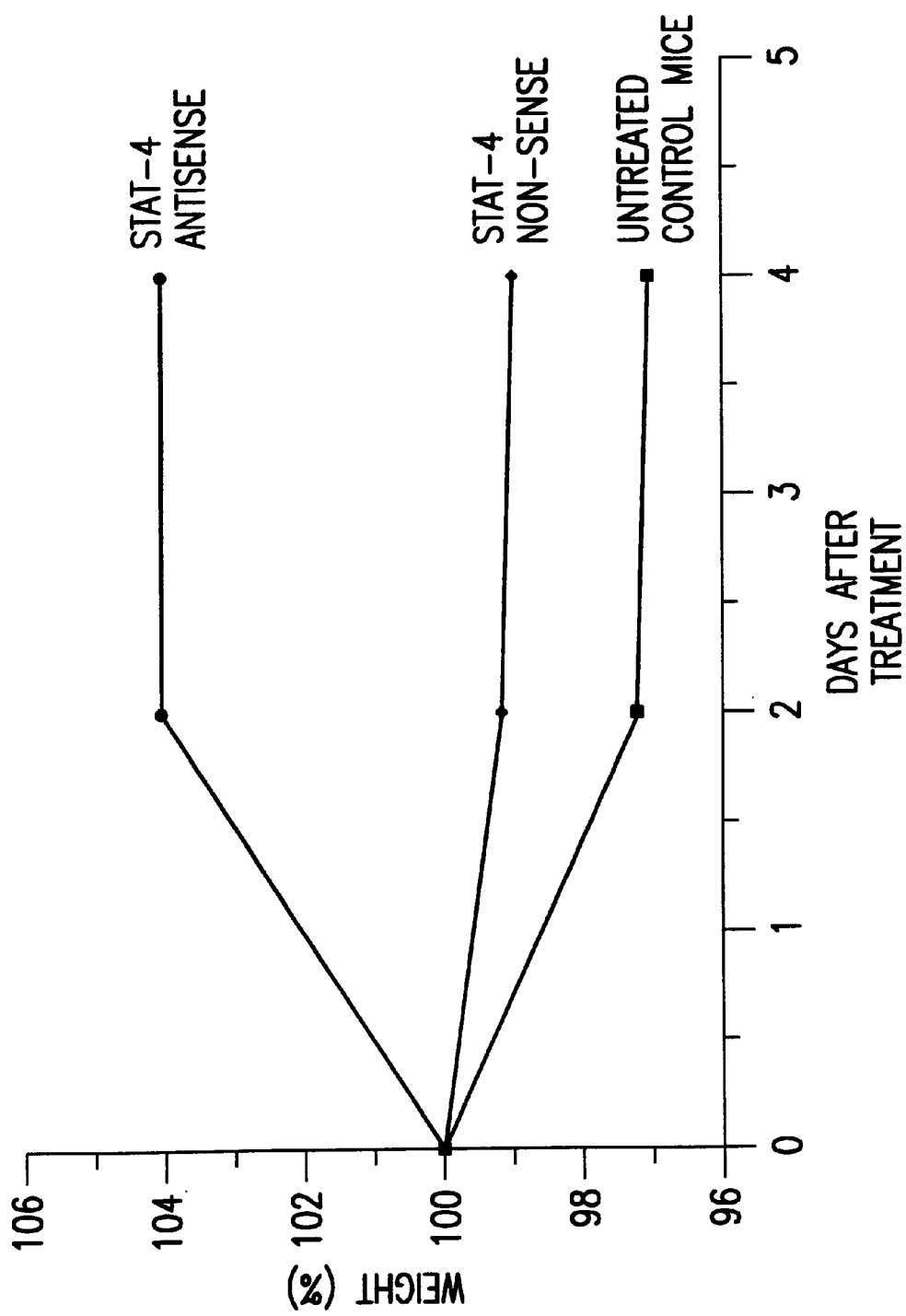
FIG. 1 shows that STAT-4 antisense-treated mice with TNBS-induced colitis, but not nonsense-treated or control mice, maintained and/or gained weight within two days after treatment with STAT-4 antisense oligonucleotide.

As used herein, "a" or "an" may mean one or more. For example, "a" cell may mean one cell or more than one cell.

The present invention provides a method of treating or preventing the inflammatory response of an inflammatory bowel disease (IBD) in a subject, comprising administering to the subject an amount of a STAT-4 antisense oligonucleotide effective in treating or preventing the inflammatory response of the IBD. Any animal which is subject to IBD can be treated by this method although humans are the primary therapeutic target. As used herein, an "inflammatory response of an IBD" refers to a condition of the colon characterized by a state of inflammation ("colitis") in which one or more of the following histological characteristics, as are well known in the art, are detectable: leukocyte infiltration; thickening of the colon wall; transmural infiltrations; loss of goblet cells; ulcerations; granulomas; and fibrosis. Clinical symptoms of an inflammatory response (colitis) of an IBD can include, but are not limited to, diarrhea, rectal prolapse, weight loss, abdominal pain, dehydration and splenomegaly.

In a preferred embodiment, the IBD of this invention is Crohn's disease. however, this invention also encompasses treatment or prevention of any IBD which produces an inflammatory response which can be treated or prevented by the administration of STAT-4 antisense oligonucleotides.

An effective amount of a STAT-4 antisense oligonucleotide is that amount which reduces or reverses the histological and clinical manifestations of the inflammation to a greater degree than observed in controls, as described herein. Specifically, the ability of a given amount of STAT-4 antisense oligonucleotide of this invention to reduce the inflammatory response of an IBD can be determined by evaluating the histological and clinical manifestations, as set forth herein, of the subject before and after administration of the oligonucleotides and quantitating the amount of reduction of the inflammation in response to given amounts. If, for a given amount, the reduction in inflammatory response is greater than the amount of reduction in inflammatory response in a control subject, then the amount of STAT-4 antisense oligonucleotide administered to achieve such reduction is determined to be an amount effective in reducing the inflammatory response of an IBD.

Antisense technology is well known in the art and describes a mechanism hereby a nucleic acid comprising a nucleotide sequence which is in a complementary, "antisense" orientation with respect to a coding or "sense" sequence of an endogenous gene, is introduced into a cell, whereby a duplex forms between the antisense sequence and its complementary sense sequence. The formation of this duplex results in inactivation of the endogenous gene. Antisense nucleic acid can be produced for any endogenous gene for which the coding sequence has been or can be determined according to well known methods.

The antisense nucleic acid can inhibit gene expression by forming an RNA/RNA duplex between the antisense RNA and the RNA transcribed from a target gene. The precise mechanism by which this duplex formation decreases the production of the protein encoded by the endogenous gene most likely involves binding of complementary regions of the normal sense MRNA and the antisense RNA strand with duplex formation in a manner that blocks RNA processing and translation. Alternative mechanisms include the formation of a triplex between the antisense RNA and duplex DNA or the formation of a DNA-RNA duplex with subsequent degradation of DNA-RNA hybrids by RNAse H. Furthermore, an antisense effect can result from certain DNA-based oligonucleotides via triple-helix formation between the oligomer and double-stranded DNA which results in the repression of gene transcription.

A nucleic acid encoding an antisense RNA can be selected based on the protein desired to be inhibited or decreased in cells, by providing an RNA that will selectively bind to the cellular mRNA encoding such protein. Binding of the antisense molecule to the target mRNA incapacitates the mRNAs, thus preventing its translation into a functional protein. The antisense RNA/mRNA complexes become a target for RNAse-H and are eventually degraded by the host cell RNAse-H. Control regions, such as enhancers and promoters, can be selected for antisense RNA targeting according to the cell or tissue in which it is to be expressed, as is known in the art. Preferable antisense-encoding constructs can encode full-length complements to target sequences; however, smaller length sequences down to oligonucleotide size can be utilized.

The antisense nucleic acid of this invention can be either RNA or DNA. Antisense nucleic acids can be synthesized and used according to standard methods well known in the art (e.g., *Antisense RNA and DNA*, D. A. Melton, Ed., Cold Spring Harbor Laboratory, Cold Spring Harbor, N.Y. (1988); refs. 72, 73). Furthermore, the antisense nucleic acid of this invention can be modified by the addition of phosphorothioate groups, ester groups and/or carbohydrate groups as is known in the art (Tanaka et al., 1992. "Phenotypic conversion of SV40-inmmortalized human diploid fibroblasts to senescing cells by introduction of an antisense gene for SV40-T antigen." *Cell Structure and Function* 17:351–362; Gutierrez et al., 1997. "Antisense gene inhibition by C-5-substituted deoxyuridine-containing oligodeoxynucleotides." Biochemistry 36:743–748).

As an example, one method of constructing an antisense nucleic acid is to synthesize a recombinant antisense DNA molecule. For example, oligonucleotide synthesis procedures are routine in the art and oligonucleotides coding for a particular protein or regulatory region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins or regulatory regions can be synthesized by first constructing several different double-stranded molecules that code for particular regions of the protein or regulatory region, followed by ligating these DNA molecules together. For example, Cunningham, et al., "Receptor and Antibody Epitopes in Human Growth Hormone Identified by Homolog-Scanning Mutagenesis," *Science*, Vol. 243, pp. 1330–1336 (1989), describes the construction of a synthetic gene encoding the human growth hormone gene by first constructing overlapping and complementary synthetic oligonucleotides and ligating these fragments together. See also, Ferretti, et al., Proc. Nat. Acad. Sci. 82:599–603 (1986), wherein synthesis of a 1057 base pair synthetic bovine rhodopsin gene from synthetic oligonucleotides is disclosed. Once the appropriate DNA molecule is synthesized, this DNA can be cloned downstream of a promoter in an antisense orientation. Techniques such as this are routine in the art and are well documented.

Another method of obtaining an antisense nucleic acid is to isolate that nucleic acid from the cell in which it is found and clone it in an antisense orientation. For example, a DNA or cDNA library can be constructed and screened for the presence of the nucleic acid of interest. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector in an antisense orientation, or if necessary, be modified to facilitate the subsequent cloning steps. Such modification steps are routine, an example of which is the addition of oligonucleotide linkers which contain restriction sites to the termnini of the nucleic acid. General methods are set forth in Sambrook et al., "Molecular Cloning, a Laboratory Manual," Cold Spring Harbor Laboratory Press (1989).

The antisense nucleic acids can be administered to the cells of the subject either in vivo and/or ex vivo. If ex vivo methods are employed, cells or tissues can be removed and maintained outside the body according to standard protocols well known in the art. The nucleic acids of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

For in vivo methods, the antisense nucleic acid can be administered to the subject in a pharmaceutically acceptable carrier as further described below.

In the methods described above which include the administration and uptake of antisense nucleic acid into the cells of a subject (i.e., gene transduction or transfection), the antisense nucleic acids of the present invention can be in the form of naked nucleic acid or the nucleic acids can be in a vector. The vector can contain the antisense nucleic acid in antisense orientation or in the complementary orientation so that the antisense sequence is expressed from the vector. The vector can be a commercially available preparation, such as an adenovirus vector (Quantum Biotechnologies, Inc. (Laval, Quebec, Canada).

Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., 62, 63). The recombinant retrovirus can then be used to infect and thereby deliver to the infected cells antisense nucleic acid. The exact method of introducing the antisense nucleic acid into mammalian cells is, of course, not limited to the use of retroviral vectors. Other techniques are widely available for this procedure including the use of adenoviral vectors (64), adeno-associated viral (AAV) vectors (65), lentiviral vectors (66), pseudotyped retroviral vectors (67). Physical transduction techniques can also be used, such as liposome delivery and receptor-mediated and other endocytosis mechanisms (see, for example, 68). This invention can be used in conjunction with any of these or other commonly used gene transfer methods.

Also provided by this invention is an isolated nucleic acid encoding a STAT-4 antisense oligonucleotide and/or a recombinant nucleic acid comprising a nucleic acid encoding a STAT-4 antisense oligonucleotide in a vector. The vector can be present in a cell, which can be an in vivo cell, an ex vivo cell, a cell cultured in vitro or a cell in a transgenic animal. The vector can also be a regulatable vector such as a tetracycline inducible vector, see Schultze et al. "Efficient control of gene expression by single step integration of the tetracycline system in transgenic mice." Nat. Biotech. 14:499–503 (1996).

It is also contemplated in this invention that transgenic animals can be produced which produce antisense STAT-4 oligonucleotides. For example, a transgenic animal which produces the antisense oligonucleotides of this invention can be produced according to the methods taught in the Examples, as well as by methods well known in the art whereby nucleic acid encoding an antisense STAT-4 oligonucleotide is introduced into embryonic stem cells, at which stage it is incorporated into the germline of the animal, resulting in the production of antisense STAT-4 oligonucleotide in the transgenic animal.

As described above, the antisense nucleic acid or vector of the present invention can be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The nucleic acid or vector may be administered orally, parenterally (e.g., intravenously), by intramuscular injection, by intraperitoneal injection, transdermally, extracorporeally, intrarectally, topically or the like, although intravenous and/or intrarectal administration is typically preferred. The exact amount of the nucleic acid or vector required will vary from subject to subject, depending on the species, age, weight and general condition of the subject, the severity of the disease being treated, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein (see, e.g., Remington's Pharmaceutical Sciences; ref 70).

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Suitable carriers for use in the present invention include, but are not limited to, pyrogen-free saline. For parenteral administration, a sterile solution or suspension is prepared in-saline that may contain additives, such as ethyl oleate or isopropyl myristate, and can be injected, for example, into subcutaneous or intramuscular tissues.

Suitable carriers for oral administration of antisense nucleic acids include one or more substances which may also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pharmaceutically accepted oils, or a mixture of both. The liquid can also contain other suitable pharmaceutical additions such as buffers, preservatives, flavoring agents, viscosity or osmoregulators, stabilizers or suspending agents. Examples of suitable liquid carriers include water with or without various additives, including carboxypolymethylene as a pH-regulated gel.

As one example, treatment of an inflammatory response of an IBD in a subject can consist of a single intravenous dose of from about 0.5 to about 5.0 mg/kg of body weight of STAT-4 antisense oligonucleotides. For intrarectal administration, a dosage approximately one fifth of the intravenous dosage is typical, e.g., in a range of from about 0.1 to 1.0 mg/kg of body weight of STAT-4 antisense oligonucleotides.

As another example, if the nucleic acid of this invention is delivered to the cells of a subject in an adenovirus vector, the dosage for administration of adenovirus to humans can range from about $10^7$ to $10^9$ plaque forming unit (pfu) per injection but can be as high as $10^{12}$ pfu per injection (60, 61). Ideally, a subject will receive a single injection. If additional injections are necessary, they can be repeated at six month intervals for an indefinite period and/or until the efficacy of the treatment has been established.

Subjects can be given a laboratory evaluation consisting of a complete blood count (CBC) with differential, platelet count, SMA-18 chemistry profile, erythrocyte sedimentation rate (ESR) and a C-reactive protein assay at 1) the time of antisense oligonucleotide administration; 2) 24 hours later; 3) 72 hours later; 4) two weeks later; 5) four weeks later; (6) six weeks later; and 7) eight weeks later, relative to the time of oligonucleotide administration.

To evaluate the efficacy of STAT-4 antisense oligonucleotide treatment in humans with IBD, the following studies are performed. Patients with active inflammation of the colon and/or the terminal ileum who have failed standard prednisone therapy (parenterally or orally) for control of the IBD are selected. Drug efficacy is monitored via colonoscopy. Patients are randomized to two different protocols. In one protocol, subjects remain on initial steroid dosage and in the second protocol, subjects have their steroid dosage tapered after receiving STAT-4 antisense therapy. Subjects also undergo routine colonoscopy with video surveillance at the time of the antisense oligonucleotide administration and again two, four, six and eight weeks later.

Additionally, serum samples from the subjects are assayed by ELISA for IFN-γ levels to monitor drug efficacy. Also, tissue biopsy samples obtained during colonoscopy are cultured and assayed for IFN-γ levels.

The present invention also provides a STAT-4 antisense oligonucleotide having the nucleotide sequence of SEQ ID NO:7, as well as any other STAT-4 antisense oligonucleotide identified to have the inflammation inhibitory effects of the oligonucleotide of SEQ ID NO:7.

The present invention is more particularly described in the following examples which are intended as illustrative only since numerous modifications and variations therein will be apparent to those skilled in the art.

EXAMPLES

Patients. Colonic specimens obtained from 35 surgical patients admitted for bowel resection were studied. Whereas the Crohn's disease (CD) group consisted of 4 men and 11 women, ranging from 19 to 66 years of age, the ulcerative colitis (UC) group consisted of 2 men and 8 women, ranging from 23 to 55 years of age. In some cases (n=2) addition, macroscopically uninvolved tissue from patients with CD was obtained. The diagnosis for each patients was made using clinical parameters, radiographic studies, and histologic criteria. At the time of resection, 7 patients of the CD group were receiving corticosteroids, 1 patient was receiving an oral sulfasalazine preparation, and 7 patients were on no medications. In the UC group, 4 patients were receiving corticosteroids, 1 oral sulfasalazine and 5 were on no medications. The control group consisted of colonic specimens from 15 patients admitted for therapeutic bowel resection for malignant (adenocarcinoma; n=13) and nonmalignant (diverticulosis; n=2) conditions. There were 2 male and 13 female patients in the control group ranging from 36 to 92 years of age. These patients were not receiving sulfasalazine or corticosteroids at the time of the resection.

Isolation of human lamina propria macrophages and CD4+ T cells. Lamina propria (LP) mononuclear cells (LPMC) were isolated using a previously described technique (31). LP macrophages were then enriched from the resultant cell population by negative selection techniques using monoclonal antibodies attached to immunomagnetic beads (9, 32). The resultant cell population was more than 90% positive for MAC1, as assessed by FACS analysis. Cell viability was determined by trypan blue exclusion (TBE) and was higher than 95% in all experiments. In some control experiments, peripheral blood monocytes from healthy volunteers were prepared using the same procedure. LP CD4+ T cells were prepared from LPMC by negative selection techniques using monoclonal antibodies attached to immunomagnetic beads (9). In brief, cell populations were suspended at $2\times10^7$ cells/ml in calcium-free PBS with 1% FCS to which a 1:350 dilution of ascites fluid containing antibodies to CD8 (OKT8; Ortho), CD14, CD16, CD20 (Leu16; Becton Dickinson), anti-glycophorin (10F7; ATCC) or anti-erythroglycoprotein was added. The cells were incubated at 4° C. for 30 min, washed twice and resuspended in coating medium. The antibody coated cell populations were then removed by an initial incubation with immunomagnetic beads coated with anti-murine IgG antibody (Advanced Magnetics, Cambridge, Mass.) followed by a subsequent incubation with immunomagnetic beads coated with anti-murine IgG antibody obtained from Dynal (Oslo, Norway). The resultant cells were more than 90% CD4+ by FACS analysis. Cell viability was higher than 93% in all experiments, as assessed by TBE.

Polymerase chain reaction. Total cellular RNA from LP cells was isolated by the acid guanidium thiocyanate-phenol-chloroform extraction method. Reverse transcriptase reaction of heat-denatured total RNA with Moloney murine leukemia virus reverse transcriptase was performed according to the manufacturer's protocol (Life Technologies). From the obtained cDNA, β-actin and the IL-12R β1 and β2 chains were amplified by polymerase chain reaction (PCR) (denaturation 94° C. for 1 min, 55° C. for 2 min, 72° C. for 2 min for 35 cycles; final extension 72° C. for 10 min) using specific primers derived from previously published sequence data. PCR probes were analyzed on 2% agarose gels.

Preparation of nuclear extracts. Small-scale extractions of nuclear proteins ("mini-extracts") from LP CD4+ T lymphocytes were performed as previously described (32). Protein concentrations were measured with the Bradford assay using Coomassie blue as a reagent.

Electrophoretic mobility shift assays (EMSAs). Binding reactions (15 μl) for EMSA contained 2 μg synthetic DNA duplex of poly (dI-dC) (Pharmacia Fine Chemicals, Piscataway, N.J.), 25000 cpm (Cerenkov) of end-labeled DNA probe, 20 μg nuclear proteins and incubation buffer (10 mM HEPES, pH 7.9, 100 mM NaCl, 10% glycerol, 0.5 mM $MgC_2$, 1 mM DTT). After preincubation without DNA for 15 minutes at room temperature, end-labeled DNA probe was added to the reaction for an additional 15 minutes and complexes were separated from unbound specific probe by electrophoresis in native 4% polyacrylamide gels. After electrophoresis, the gels were dried and exposed to Kodak films on intensifying screens overnight at −80° C. The sequences for the STAT DNA probes were as follows:

Western blot analysis. Nuclear extracts from T cells were isolated and analyzed by SDS/PAGE (10% acrylamide gels) followed by blotting with rabbit anti-NF-kB p50, anti-STAT-1, anti-STAT-4 or anti-STAT-6 antibodies (Santa Cruz Biotechnology, Calif.) and immunodetection was performed as previously described (32). Gels were analyzed by densitometry as described herein.

Phosphorothioate oligonucleotides. Phosphorothioate antisense oligonucleotides consisted of 21-mer analogues to the 5' end of human STAT-4 (gene bank accession number L78440) which span the translation initiation site. In addition, mismatched and control (non-sense) oligonucleotides were prepared, the latter consisting of 21-mers containing the same nucleotide composition of the anti-sense oligonucleotide. The sequences of the phosphorothioate oligonucleotides were as follows:

STAT-4 antisense: 5'-TTCCACTGAGACATGCTAGCG-3' (SEQ ID NO:7)

STAT-4 mismatched: 5'-TTCTACTGCGACATGATAGCG-3' (SEQ ID NO:8)

STAT-4 nonsense" 5'-ATATCCGCGTATGCATCGAGC-3' (SEQ ID NO:9)

In co-incubation studies, phosphorothioate oligonucleotides were added at a final concentration of 8 μM to the culture medium.

Cell-culture of lamina propria macrophages. Cell cultures of monocytes/macrophages were established in complete medium consisting of RPMI-1640 supplemented with 3 mM L-glutamine, 10 mM HEPES buffer, 10 μg/ml gentamycin (Whittaker), 100 U/ml each of penicillin and streptomycin (Whittaker), 0.05 mM 2ME (Sigma Chemical) and 10% heat-inactivated fetal calf serum. To some of the samples, 40 μg/ml bacterial lipopolysaccharide (Sigma Chem., St. Louis), 0.07% v/v staphylococcus aureus Cowan's antigen (SAC; Sigma Chem.), 10 μg/ml to IL-10 or CD40L (Pharmingen) or 10 U/ml recombinant IFN-γ (R&D systems) were added as described herein. To stimulate monocytes/macrophages via the CD40/CD40L interaction, $1 \times 10^6$ monocytes/macrophages were co-incubated with $2 \times 10^5$ CD40L-expressing CD232 (FcγRII)-transfected L cells for 48 hours. Co-incubation with oligonucleotides was performed by adding indicated amounts of oligonucleotides to the cell culture.

Cytokine Assays. $1 \times 10^6$ purified monocytes/macrophages or CD4+ T cells were cultured in 24-well plates in 1 ml complete medium. To measure cytokine production, cultures were incubated in 24-well plates (Costar) at 37° C. in a humidified incubator containing 6% $CO_2$. After 24 hours (monocytes/macrophages) or 48 hours (T cells), supernatants were removed and assayed for cytokine concentration. Cytokine concentrations of IL-12 p70, IFN-γ and IL-4 were determined by specific ELISA according to the manufacturer's recommendations (Pharmingen or R&D Systems, Minneapolis, Minn.). Optical densities were measured on a Dynatech MR 5000 ELISA reader at a wavelength of 490 nm.

Immunohistochemistry. For immunohistochemistry, 10 μm thick cryosections were prepared, dried, and fixed in 4% paraformaldehyde (PFA) and washed in 0.01M phosphate buffered saline (PBS, pH 7.4). Sections were then pre-treated with 10% of serum (corresponding to the secondary antibody) in PBS/0.1% TritonX-100 and incubated overnight at 4° C. with the primary antibody (10 μg/ml; monoclonal mouse anti-STAT-4; obtained from Santa Cruz, Heidelberg; or monoclonal mouse anti-IL-12; obtained from R&D Systems). The following day, sections were rinsed in PBS and incubated with a biotinylated secondary IgG antibody (1:100 dilution; obtained from Vector, Burlingame, Calif.) for 1 hour at room temperature followed by incubation with streptavidin conjugated Cy2 (Dianova, Hamburg, Germany) (1:500) for 2 hours at room temperature. For double staining, sections were rinsed with PBS and subjected to a second cycle of staining using anti-CD4 as primary antibody (10 μg/ml) and streptavidin-conjugated Cya as chromogen. Finally, slides were mounted with mounting medium for fluorescence (Vector, Burlingame, Calif.) and analyzed with an Olympus Microscope (Olympus U-MCB; AX70) for double immunofluorescence.

Quantitative immunofluorescence. Quantification of STAT-4 or IL-12 positive T cells was performed on doubled-stained cryostat sections in 7 patients of each group (control and CD patients) by examining 10 randomly selected high power fields (HPF). Under these experimental conditions, one HPF represented 0.25 $mm^2$. Samples incubated with isotype-matched control antibodies and without primary antibody served as negative controls.

Statistical analysis. ELISA data were compared using the Wilcoxon test and the program Statworks for Macintosh.

Lamina Propria IL-12 Production in IBD: Qualitative and Quantitative Detection of IL-12-specific Cells by Immunofluorescence Staining of Tissue Cryosections. The in vivo levels of IL-12 in the laminapropria of patients with inflammatory bowel disease were determined. Fresh tissue specimens were obtained from groups of patients with Crohn's disease (CD), patients with ulcerative colitis (UC), and controls as described herein and cryosections of the tissues were probed for the presence of IL-12 using an IL-12-specific immunofluorescence staining technique. Patient tissues examined were obtained from active areas of inflammation in each case.

The tissue obtained from each of the patients with CD contained many IL-12-positive cells, whereas the tissue obtained from control individuals and patients with ulcerative colitis contained only a few IL-12-positive cells. In addition, staining of tissue with a control IgG antibody was negative in each group. These findings were confirmed by studies in which IL-12 p70-positive cells in the lamina propria were enumerated by counting positive cells in 10 randomly selected high powered fields (HPF). These studies showed that the number of IL-12 p70 expressing cells was significantly ($p<0.05$) increased in CD tissue (15.4±0.3 positive cells/HPF), as compared to both ulcerative colitis tissue (1.9±2.1 cells/HPF) and control tissue (3.0±2.8 cells/HPF). These data demonstrate that in situ IL-12 production was qualitatively increased in the lamina propria of Crohn's disease patients compared to that in the lamina propria of either ulcerative colitis patients or controls.

Lamina Propria IL-12 Production in IBD: Quantitative Detection by Measurement of CD40L-stimulated Monocyte/Macrophage Production of IL-12 in vitro. To obtain a more precise estimate of lamina propria (LP) IL-12 production in IBD, IL-12 production was measured in stimulated monocytes/macrophages extracted from specimens of gut tissues from patients and control individuals. In initial studies, monocytes/macrophages from both peripheral blood and gut tissues were cultured with various potential stimulants to induce IL-12 production. Culture supernatants were assayed for IL-12 using an ELISA specific for heterodimeric IL-12 (IL-12 p70). LP monocytes/macrophages stimulated with SAC, LPS, or SAC plus LPS produced low amounts of IL-12 compared to PB monocytes. In contrast, LP monocytes/macrophages stimulated with CD40L and CD40L plus IFN-γ produced relatively high amounts of IL-12 compared to PB cells. Such increased production was not augmented by addition of anti-IL-10, but was blocked by addition of anti-gp39 (anti-CD40L). These findings indicated that LP monocytes/macrophages require a T cell-dependent stimulus, CD40L, for optimal IL-12 production.

IL-12 production by LP monocytes/macrophages from patients with IBD was also analyzed. LP monocytes/macrophages obtained from gut specimens from patients with CD stimulated with CD40L plus IFN-γ produced strikingly increased amounts of IL-12 as compared to LP macrophages from controls (p<0.01). In contrast, LP monocytes/macrophages from UC patients produced normal or less IL-12 than control monocytes/macrophages under these stimulation conditions. LP monocytes/macrophages from CD and UC tissue produced low amounts of IL-12 when stimulated with SAC or SAC plus LPS, and these amounts were not strikingly different from that produced by control LP macrophages. Taken together with the immunofluorescence staining data described above, these data indicated that both unstimulated and stimulated IL-12 production is increased in CD lamina propria but not in UC.

Evidence that Increased IL-12 Production by CD Macrophages is Associated with Increased IL-12 Signaling via STAT-4 in CD LP T Cells. In the following series of studies, a determination was made regarding whether the increased IL-12 production by monocytes/macrophages of CD patients has functional implications, i.e., was associated with evidence of IL-12 signaling in CD LP T cells.

A. High expression of IL-12R $\beta_2$-Chain mRNA in LP T Cells from Patients with CD. The level of expression of IL-12R $\beta_1$ and $\beta_2$-chain mRNA was determined in LP T cells obtained from inflamed tissue of CD and UC patients, as well as control individuals, because, as mentioned above, IL-12 signaling requires the expression of both components of the IL-12 receptor. As shown in polymerase chain reaction studies (PCR) studies, strong signals for the IL-12R $\beta_1$-chain were obtained using cDNA from UC, CD, and control LP CD4+ T cells. In contrast, IL-12R $\beta_2$-chain signals were stronger in LP T cells obtained from patients with CD compared to UC and control patients.

B. Selective Activation of STAT-4 in LP CD4+ T Cells of Patients with CD but not Patients with UC. Detection by Electrophoretic Mobility (Gel Shift) Assays. To determine if the increased production of IL-12 in CD was associated with evidence of IL-12 signaling, CD4+ LP T cells from CD patients were analyzed for increased expression of activated STAT-4, a transcription factor specifically activated by IL-12 (26, 33). For these studies, the fact that activated STAT-4, but not non-activated STAT-4 is translocated to the cell nucleus and then binds to STAT-4-specific oligonucleotides (33–34) was taken into consideration. Accordingly, nuclear proteins were extracted from purified CD4+ T cells of inflamed CD gut tissue and electrophoretic mobility gel shift assays were performed on the extracted proteins using a labeled oligonucleotide known to bind STAT-4. The specificity of the observed retarded protein/DNA complex was shown by competition and supershift assays. The STAT-4 band was not seen after addition of STAT-4 specific antibodies and could be specifically competed by unlabeled STAT-4 but not c-maf' or NFAT' binding oligonucleotides. Gel shift assays of nuclear cell extracts from CD4+ T cells of CD patients also resulted in retarded bands, suggesting the presence of weak retarded bands.

In further analyses, immunohistochemical studies were performed to verify that increased nuclear STAT-4 levels also occur in the lamina propria of CD patients in vivo. Only a weak expression of STAT-4 in lamina propria T cells of control patients was observed. In contrast, a striking increase of STAT-4 expression was observed in both subepithelial areas and the muscularis propria in CD patients. Finally, triple staining analysis with nuclear counterstaining showed that STAT-4 expression was mainly localized in the nucleus, suggesting activation and nuclear translocation of STAT-4 in CD LP CD4+ T lymphocytes.

Downregulation of STAT-4 expression in CD LP CD4+ T cells by anti-sense oligonucleotides results in reduced IFN-$\gamma$ production. The functional role of activated STAT-4 was analyzed in LP CD4+ T cells obtained from patients with CD. In these studies, an anti-sense strategy was employed to down-regulate the intra-cellular production of STAT-4 mRNA and the effect of such down-regulation on IFN-$\gamma$ production was measured. In this approach, STAT-4 mRNA translation is disrupted with an anti-sense phosphorothioated oligonucleotide that binds to the translation start site of STAT-4. LP CD4+ T cells were stimulated with anti-CD2/anti-CD28 plus IL-12 in the presence or absence of phosphorothioated oligonucleotides that were anti-sense to the STAT-4 translation start site. After 48 hours, STAT-4 protein expression in cellular extracts was determined by Western blot.

The addition of the anti-sense oligonucleotide strongly reduced STAT-4 protein expression. In contrast, neither mismatched nor non-sense oligonucleotides had this effect. The addition of STAT-4 anti-sense oligonucleotides to cell cultures did not strongly affect cell viability, as assessed by trypan blue exclusion (88±6% versus 96±8% viable cells after 48 hours).

Having established the inhibitory effect of STAT-4 antisense oligonucleotides on STAT-4 production, the effect of STAT-4 down-regulation on LP CD4+ T cell cytokine production by cells obtained from patients with CD was analyzed. Addition of STAT-4 anti-sense oligonucleotides to cultures of anti-CD2/anti-CD28 plus IL-12-stimulated LP CD4+ T cells obtained from CD patients was accompanied by reduced secretion of IFN-$\gamma$, as detected by measurement of culture supernatant cytokines with an IFN-$\gamma$-specific ELISA. This effect was not found with the addition of the various control oligonucleotides. These data show that STAT-4 is a major regulator of IFN-$\gamma$ production by LP CD4+ T cells from patients with and that the production of IL-12 in such patients induces IFN-$\gamma$ production via its effect on STAT-4 activation.

Induction of experimental colitis. Specific pathogen-free 2–4 month old female BALB/c or SJL/J mice were obtained from the National Cancer Institute (NCI, Bethesda, Md.) and maintained in the building 10A animal facility at the National Institutes of Health. The mice were lightly anesthetized with metofane (methoxyflurane; Pitman-Moore, Mundelein Ill.). A 3.5 F catheter was inserted into the colon until the tip was 4 cm proximal to the anus. To induce colitis, 0.5 mg of the hapten reagent 2,4,6-trinitrobenzene sulfonic acid (TNBS; Sigma, St. Louis, Mo.) in 50% ethanol (to break the intestinal epithelial barrier) was slowly administered into the lumen of the colon via the catheter fitted onto a 1 ml syringe. In control experiments, mice received 50% ethanol alone using the same technique described above. The total injection volume was 100 $\mu$l in both groups, allowing TNBS or ethanol to reach the entire colon including caecum and appendix. Animals were kept in a vertical position for 30 seconds and returned to their cages.

The animal in which the colitis is produced can be any mammal and can include but is not limited to mouse, rat, guinea pig, hamster, rabbit, cat, dog, goat, monkey, and chimpanzee. The colitis can be produced in the animal by any method known in the art. For example, the colitis can be produced by introducing into the colon of the animal an effective amount of a hapten reagent. The hapten reagent can be, but is not limited to, 2,4,6-trinitrobenzene sulfonic acid, 2,4-dinitrochlorobenzene and other trinitrophenylamnine compounds.

Grading of histologic changes. Tissues were removed at various time points and embedded in paraffin. Paraffin sections were made and stained with haematoxylin and eosin. The degree of inflammation on microscopic cross sections of the colon was graded semiquantitatively from 0 to 4 [0 - no signs of inflammation, colon is indistinguishable from that of a normal colon; 1 - very low level of leucocytic infiltration (1–10% of field infiltrated with leucocytes); 2 - low level of leucocytic infiltration (11–25% of field infiltrated with leucocytes), hyperemia; 3 - high level of leucocytic infiltration (26–50% of field infiltrated with leucocytes), high vascular density, thickening of the colon wall; 4 - transmural leucocytic infiltrations (>50% of field infiltrated with leucocytes), loss of goblet cells, high vascular density, thickening of the colon wall]. Grading was done in a blinded fashion by the same pathologist.

Morphometric assessment of colon wall thickness. Three or more animals from each treatment group were randomly selected at various time points and colon samples were removed and embedded in paraffin. Thickness of the colon wall was determined on cross sections by measuring the distance from the serosal surface to the luminal surface at 2 mm intervals along the entire length of each section through a calibrated eyepiece using an Olympus Vanox S1 microscope.

Intrarectal administration of 2,4,6-trinitrobenzene sulfonic acid induces a chronic granulomatous colitis in BALB/c and SJL/J mice. BALB/c and SJL/J mice subjected to intrarectal administration of TNBS in 50% ethanol reproducibly developed pancolitis with severe diarrhea and rectal prolapse accompanied by an extensive wasting disease. The peak of clinical disease occurred at three weeks and clinical signs of colitis usually subsided after two months. Control mice treated with 50% ethanol alone failed to develop wasting disease and appeared healthy.

The colons of TNBS-treated BALB/c mice removed seven days after administration of TNBS revealed striking hyperemia and inflammation, whereas the colons of control mice treated with 50% ethanol alone showed no macroscopic signs of inflammation. In addition, TNBS-treated mice displayed splenomegaly.

In vivo data. The effect of local (intra-rectal) administration of STAT-4 antisense oligonucleotides on TNBS-induced colitis was evaluated. Mice with TNBS colitis induced as described herein were treated by local administration of STAT-4 antisense oligonucleotides or control nonsense oligonucleotides. CD4+ T cells isolated from the colons of the treated mice were cultured in vitro. Western blot and RT-PCR assays performed with these T cells demonstrated that STAT-4 expression was clearly downregulated in mice treated with STAT-4 antisense oligonucleotides but not in mice treated with nonsense oligonucleotides. This effect was specific, as the treatment with STAT-4 antisense oligonucleotides had no effect on other pro-inflammatory proteins such as IL-1β. In another series of studies, mice with TNBS colitis were treated by intra-rectal administration of STAT-4 antisense oligonucleotides or control oligonucleotides. The mice treated with STAT-4 antisense oligonucleotides manifested a cessation of diarrhea and a marked increase in weight; in addition, they showed histological abrogation of intestinal inflammation as determined according to the assays described herein. In comparison, mice treated with nonsense control oligonucleotides continued to have TNBS colitis.

Additional studies similar to those described above for TNBS colitis mice were also carried out in a SCID mouse model of colitis induced by adoptive transfer of CD62L high CD4+ T cells. The mice were grouped as STAT-4 antisense oligonucleotide; STAT-4 nonsense oligonucleotide and untreated control. Three mice in each of the oligonucleotide groups were treated by local administration of 150 µg antisense or nonsense oligonucleotides 75 days after the adoptive transfer. Antisense-treated mice, but not nonsense-treated or control mice, began to gain weight within two days after treatment (FIG. 1).

Administration of STAT-4 antisense oligonucleotides to a human subject. To inhibit the inflammatory response of an IBD in a human subject, from about 0.5 to about 5.0 mg/kg of body weight of STAT-4 antisense oligonucleotides (e.g. an oligonucleotide having the nucleotide sequence of SEQ ID NO:7 or SEQ ID NO: 10, or a functional fragment thereof) are administered intravenously as a single dose and the subject can then be evaluated for a reduction in the inflammatorey response. For intrarectal administration, from about 0.1 to 1.0 mg/kg of STAT-4 antisense oligonucleotides can be administered.

Figure 2:
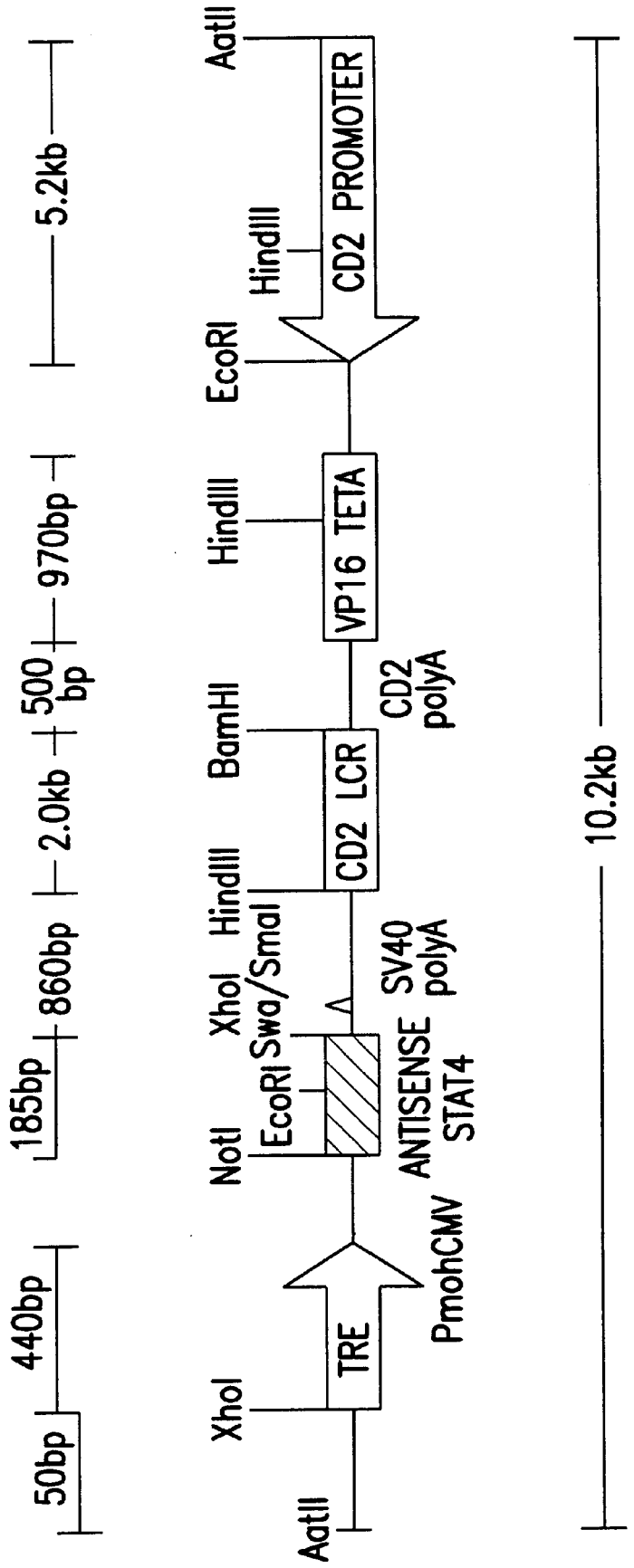
FIG. 2 shows a regulatable vector comprising a STAT-4 antisense nucleic acid.

Tetracycline-inducible antisense STAT-4 transgenic animal. A tetracycline inducible antisense STAT-4 construct was designed and constructed as shown in FIG. 2, using the antisense nucleic acid of SEQ ID NO: 10. This construct was then introduced into embryonic cells by methods for transgenesis that are standard in the art to produce a transgenic mouse that expresses an antisense STAT-4 nucleic acid. Experimental colitis was induced in these mice as described above. The antisense STAT-4 nucleic acid is produced in the transgenic animal as follows: Reverse tetracycline transactivator protein (rtTA) fused with VP16 is produced by the CD2 promoter, a T cell specific promoter. Once rtTA-VP16 is produced, rtTA-VP16 binds to the tetracycline responsible element (TRE) in the presence of doxycycline which is supplied to the transgenic mouse through a drinking water solution and activates the mini CMV promoter, which then transcribes the antisense sequence for STAT-4. Studies utilizing this mouse system showed that TNBS induced colitis was reduced, as determined by measurement of body weight, histological examination of intestinal tissue and measurement of IFN-γ by intestinal lymphocytes, as a result of a decrease in transcription and/or translation of cellular STAT-4 mRNA in the presence of an antisense STAT-4 nucleic acid. Specifically, the antisense STAT-4 transgenic mice that had developed TNBS induced colitis and were subsequently induced to express the antisense STAT-4 nucleic acid, showed maintained and/or increased body weight when compared to antisense STAT-4 transgenic mice that had developed TNBS induced colitis and were not subsequently induced to express the antisense STAT-4 nucleic acid and in which body weight decreased.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties, as well as the references cited in these publications, are hereby incorporated by reference into this application in order to more fully describe the state of the art to which this invention pertains.

REFERENCES

1. Strober, W., and M. F. Neurath. 1995. Immunological diseases of the gastrointestinal tract. In: R. R. Rich (ed) *Clinical Immunology*, Chapter 94.

Mosby, St. Louis: 1401–1428.

2. Strober, W., and R. O. Ehrhardt. Ehrhardt. 1993. Chronic intestinal inflammation: an unexpected outcome on cytokine or T cell receptor mutant mice. *Cell* 75: 203–205 (1993).

3. Toy, L. S., and L. Mayer. 1996. Basic and clinical overview of the mucosal immune system. *Semin. Gastrointest. Dis.* 7: 2–11.

4. Probert, C. S., A. Chott, J. R. Turner, L. J. Saubermann, A. C. Stevens, K. Bodinaku, C. O. Elson, S. P. Balk, and R. S. Blumberg. 1996. Persistent clonal expansions of peripheral blood CD4+ lymphocytes in chronic inflammatory bowel disease. *J. Immunol.* 157: 3183–3191.

5. Toy, L. S., X. Y. Yio, A. Lin, S. Honig, and L. Mayer. 1997. Defective expression of gp180, a novel CD8 ligand on intestinal epithelial cells, an inflammatory bowel disease. *J. Clin. Invest.* 100: 2062–2071.

6. Powrie, F., M. W. Leach, S. Mauze, S. Menon, L. B. Caddle, and R. L. Coffman. 1994. Inhibition of Th1 responses prevents inflammatory bowel disease in scid mice reconstituted with CD45Rbhi CD4+ T cells. *Immunity* 2: 553–562.

7. Neurath, M. F., I. Fuss, B. L. Kelsall, E. Stuber, and W. Strober. 1995. Antibodies to IL-12 abrogate established experimental colitis in mice. *J. Exp. Med.* 182: 1280–1289.

8. Stuber, E., W. Strober, and M. F. Neurath. 1996. Blocking the CD40L-CD40 interaction in vivo specifically prevents the priming of Th1-T cells through the inhibition of IL-12 secretion. *J. Exp. Med.* 183: 693–698.

9. Fuss, I., M. Neurath, M. Boirivant, J. S. Klein, C. De la Motte, S. A. Strong, C. Fiocchi, and W. Strober. 1996. Disparate CD4+ lamina propria (LP) lymphocyte secretion profiles in inflammatory bowel disease. *J. Immunol.* 157: 1261–1270.

10. Elson, C. O., R. B. Sartor, G. S. Tennyson, and R. H. Riddell. 1995. Experimental models of inflammatory bowel disease. *Gastroenterology.* 109: 1344–1367.

11. Ehrhardt, R. O., B. R. Ludviksson, B. Gray, M. Neurath, and W. Strober. 1997. Induction and prevention of colonic inflammation in IL-2-deficient mice. *J. Immunol.* 158: 566–573.

12. Ludviksson, B. R., R. O. Ehrhardt, and W. Strober. 1997. TGF-beta production regulates the development of the 2,4,6-trinitrophenol-conjugated keyhole limpet hemocyanin-induced colonic inflammation in IL-2-deficient mice. *J. Immunol.* 159: 3622–3628.

13. Groux, H. A., A. O'Garra, M. Bigler, M. Rouleau, S. Antonenko, J. de Vries, and M. G. Roncarlo. 1997. A CD4+ T-cell subset inhibits antigen-specific T-cell responses and prevents colitis. *Nature* 389: 737–742.

14. Powrie, F., J. Carlino, M. W. Leach, S. Mauze, and R. L. Coffman. 1996. A critical role for transforming growth factor-beta but not interleukin-4 in the suppression of T helper type 1-mediated colitis by CD45Rb(low) CD4+ T cells. *J. Exp. Med.* 183: 2669–2674.

15. Neurath, M. F., I. Fuss, B. L. Kelsall, D. H. Presky, W. Waegell, and W. Strober. 1996. Experimental granulomatous colitis in mice is abrogated by induction of TGF-β-mediated oral tolerance. *J. Exp. Med.* 183 (1996): 2515–2527.

16. Strober, W., B. Kelsall, I. Fuss, T. Marth, B. Ludviksson, R. Ehrhardt, and M. Neurath. 1997. Reciprocal IFN-gamma and TGF-beta responses regulate the occurrence of mucosal inflammation. *Immunol Today.* 18: 61–64.

17. Trinchieri, G. 1994. Interleukin-12: a cytokine produced by antigen-presenting cells with immunoregulatory functions in the generation of T-helper cells type 1 and cytotoxic lymphocytes. *Blood.* 84: 4008–4027.

18. Monteleone, G., L. Biancone, R. Marasco, G. Morrone, 0. Marasco, F. Luzza, and F. Pallone. 1997. Interleukin-12 is expressed and actively released by Crohn's disease intestinal lamina propria mononuclear cells. *Gastroenterology.* 112:1169–1178.

19. Seder, R. A., R. Gazzinelli, A. Sher, and W. E. Paul. 1993. IL-12 acts directly on CD4+ T cells to enhance priming for IFN-gamma production and diminishes IL-4 inhibition of such priming. *Proc. Natl. Acad. Sci. USA.* 90: 10188–10192.

20. Kubin, M., M. Kamoun, and G. Trinchieri. 1994. Interleukin-12 synergizes with B7/CD28 interaction in inducing efficient proliferation and cytokine production of human T cells. *J. Exp. Med.* 180: 211–222.

21. Trembleau, S., G. Penna, S. Gregori, M. K. Gately, and L. Adorini. 1997. Deviation of pancreas-infiltrating cells to Th2 by interleukin-12 antagonist administration inhibits autoimmune diabetes. *Eur. J. Immunol.* 27: 2330–2339.

22. Szabo, S. J., N. G. Jacobson, A. S. Dighe, U. Gubler, and K. M. Murphy. 1995. Developmental commitment to the Th2 lineage by extinction of IL-12 signaling. *Immunity.* 2: 665–675.

23. Presky, D. H., H. Yang, L. J. Minetti, A. O. Chua, N. Nabavi, C. Y. Wu, M. K. Gately, and U. Gubler. 1996. A functional interleukin-12 receptor complex is composed of two beta type cytokine receptor subunits. *Proc. Natl. Acad. Sci. USA.* 93: 14002–14007.

24. Szabo, S. J., A. S. Dighe, U. Gubler, and K. M. Murphy. 1997. Regulation of the interleukin (IL)-12R beta 2 subunit expression in developing T helper 1 (Th1) and Th2 cells. *J. Exp. Med.* 185: 817–824.

25. Rogge, L., L. Barberis-Maino, M. Biffi, N. Passini, D. H. Presky, U. Gubler, and F. Sinigagli. 1997. Selective expression of an interleukin-12 receptor component by human T helper 1 cells. *J. Exp. Med.* 185: 825–831.

26. Sangster, M. Y., D. A. Vignali, P. C. Doherty, G. C. Grosvel, and J. N. Ihle. 1996. Requirement for STAT-4 interleukin-12-mediated responses of natural killer and T cells. *Nature.* 382: 171–174.

27. Leonard, W. J. 1996. STATs and cytokine specificity. *Nat. Med.* 2: 968–969.

28. Xu, X., Y. L. Sun, and T. Hoey. 1996. Cooperative DNA binding and sequence-selection recognition conferred by the STAT amino-terminal domain. *Science.* 273: 794–797.

29. Kaplan, M. H., Y. L. Sun, T. Hoey, and M. J. Grusby. 1996. Impaired IL-12 responses and enhanced development of Th2 cells in STAT-4-deficient mice. *Nature.* 382: 174–177.

30. Magram, J., S. E. Connaughton, R. R. Warrier, D. M. Carvajal, C. Y. Wu, J. Ferrante, C. Stewart, U. Sarmiento, D. A. Faherty, and M. K. Gately. 1996. IL-12-deficient mice are defective in IFN-gamma production and type 1 cytokine responses. *Immunity.* 4: 471–481.

31. Bull, D. M., and M. A. Bookman. 1977. Isolation and functional characterization of human intestinal mucosal mononuclear cells. *J. Clin. Invest.* 59: 966–974.

32. Neurath, M. F., S. Pettersson, K. H. Meyer zum Buschenfelde, and W. Strober. 1996. Local administration of antisense phosphorothioate oligonucleotides to the p65 subunit of NF-kappaB abrogates established experimental colitis in mice. *Nature Med.* 2: 998–1004.

33. Jacobson, N. G., S. J. Szabo, R. M. Weber-Nordt, Z. Zhong, R. D. Schreiber, J. E. Darnell, and K. M. Murphy. 1995. Interleukin-12 signaling in T helper 1 (Th1) cells involves tyrosine phosphorylation of signal transducer and activator of transcription (STAT)3 and STAT4. *J. Exp. Med.* 181: 1755–1762.

34. Yamamoto, K., F. W. Quelle, W. E. Thierfelder, B. K. Kreider, D. J. Gilbert, N. A. Jenkins, N. G. Copeland, O. Silvennoinen, and J. N. Ihle. 1994. STAT4, a novel gamma interferon activation site-binding protein expressed in early myeloid differentiation. *Mol. Cell. Biol.* 14: 4342–4349.

35. Darnell, J. E., I. M. Kerr, and G. R. Stark. 1994. Jak-STAT pathways and transcriptional activation in response to IFNs and other extracellular signaling proteins. *Science.* 264: 1415–1421.

36. Sadowski, H. B., K. Shuai, J. E. Darnell, and M. Z. Gilman. 1993. A common nuclear signal transduction pathway activated by growth factor and cytokine receptors. *Science.* 261: 1739–1744.

37. Hou, J., U. Schindler, W. J. Henzel, T. C. Ho, M. Brasseur, and S. L. McKnight. 1994. An interleukin-4-induced transcription factor: IL-4 STAT. *Science.* 265: 1701–1706.

38. Abreu-Martin, M. T., and S. R. Targan. 1996. Regulation of immune responses of the intestinal mucosa. *Crit. Rev. Immunol.* 16: 277–309.

39. Targan, S. R., S. B. Hanauer, S. J. Van Deventer, L. Mayer, D. H. Present, T. Braakman, K. L. De Woody, T. F. Schaible, and P. J. Rutgeerts. 1997. A short-term study of chimeric monoclonal antibody cA2 to tumor necrosis factor alpha for Crohn's disease. *New. Engl. J. Med.* 337: 1029–1035.

40. Breese, E., and T. T. MacDonald. 1995. TNF-alpha secreting cells in normal and disease human intestine. *Adv. Exp. Med. Biol.* 371B: 821–824.

41. Breese, E., C. P. Braegger, C. J. Corrigan, J. A. Walker-Smnith, and T. T. MacDonald. 1993. Interleukin-2 and interferon-gamma secreting T cells in normal and diseased human intestinal mucosa. *Immunology.* 78: 127–131.

42. D'Andrea, A., X. Ma, M. Aste-Amezaga, C. Paganin, and G. Trinchieri. 1995. Stimulatory and inhibitory effects of interleukin (IL)-4 and IL-13 on the production of cytokines by human peripheral blood mononuclear cells: priming for IL-12 and tumor necrosis factor alpha production. *J. Exp. Med.* 181: 537–546.

43. Rugtveit, J., P. Brandtzaeg, T. S. Halstensen, O. Fausa, and H. Scott. 1994. Increased macrophage subset in inflammatory bowel disease: apparent recruitment from peripheral blood monocytes. *Gut.* 35: 669–674.

44. Stout, R. D., J. Suttles, J. Xu, I. S. Grewal, and R. A. Flavell. 1996. Impaired T cell-mediated macrophage activation in CD40 ligand-deficient mice. *J. Immunol.* 156: 8–11.

45. Thierfelder, W. E., J. M. van Deursen, K. Yamamoto, R. A. Tripp, S. R. Sarawar, R. T. Carson, A. K. Abbas, K. M. Murphy, and A. Sher. 1996. Functional diversity of helper T lymphocytes. *Nature.* 383: 787–793.

46. Scoong, L., J. C. Xu, I. S. Grewal, P. Kima, J. Sun, B. J. Longley, N. H. Ruddle, D. McMahon-Pratt, and R. A. Flavell. 1996. Disruption of CD40/CD40L interactions results in an enhanced susceptibility to Leishmania amazonensis infection. *Immunity.* 4: 263–273.

47. Adorini, L., and F. Sinigaglia. 1997. Pathogenesis and immunotherapy of autoimmune diseases. *Immunol. Today.* 18: 209–211.

48. Wu, C., J. Ferrante, M. K. Gately, and J. Magram. 1997. Characterization of IL-12 receptor beta 1 chain (IL-12Rbeta1)-deficient mice: IL-12Rbeta1 is an essential component of the functional mouse IL-12 receptor. *J. Immunol.* 159: 1658–1665.

49. O'Shea, J. J. 1997. Jaks, STATs, cytokine signal transduction, and immunoregulation: are we there yet? *Immunity.* 7:1–11.

50. Leung, S., X. Li. G. R. Stark. STATs find that hanging together can be stimulating. *Science.* 273: 750–751.

51. Zhong, Z., Z. Wen, and J. E. Darnell. 1995. STAT3 and STAT4: members of the family of signal transducers and activators of transcription. *Proc. Natl. Acad. Sci. USA.* 91: 4806–4810.

52. Meraz, M. A., J. M. White, K. C. Sheehan, E. A. Bach, S. J. Rodig, A. S. Dighe, D. H. Kaplan, J. K. Riley, A. C. Greenlund, D. Campbell, K. Carver-Moore, R. N. DuBois, R. Clark, M. Aguet, and R. D. Schreiber. 1996. Targeted disruption of the STAT1 gene in mice reveals unexpected physiologic specificity in the JAK-STAT signaling pathway. *Cell.* 84: 431–442.

53. Durbin, J. E., R. Hackenmiller, M. C. Simon, and D. E. Levy. 1996. Targeted disruption of the mouse STAT1 gene results in compromised innate immunity to viral disease. *Cell.* 84: 443–450.

54. Kaplan, M. H., U. Schindler, S. T. Smiley, and M. J. Grusby. 1996. STAT6 is required for mediating responses to IL-4 and for development of Th2 cells. *Immunity.* 4: 313–319.

55. Bacon, C. M., D. W. McVicar, J. R. Ortaldo, R. C. Rees, J. J. O'Shea, and J. A. Johnston. 1995. Interleukin-12 (IL-21) induces tyrosine phosphorylation of JAK2 and TYK2: differential use of Janus family tyrosine kinases by IL-2 and IL-12. *J. Exp. Med.* 181: 399–404.

56. Christ, A. D., A. C. Stevens, H. Koeppen, S. Walsh, F. Omata, O. Devergne, M. Birkenbach, and R. S. Blumberg. 1998. An interleukin-12-related cytokine is up-regulated in ulcerative colitis but not in Crohn's disease. *Gastroenterology.* 115: 307–313.

57. Pallone, F., and G. Monteleone. 1998. Interleukin-12 and Th1 responses in inflammatory bowel disease. *Gut.* 43: 735–736.

58. Wirtz, S., S. Finotto, S. Kanzler, A. W. Lohse, M. Blessing, H. A. Lehr, P. R. Galle, and M. F. Neurath. 1999. Cutting Edge: Chronic intestinal inflammation in STAT-4 transgenic mice: Characterization of disease and adoptive transfer by TNF-plus IFN-γ-producing CD4+ T cells that respond to bacterial antigens. *J. Immunol.* In press.

59. Podolsky, D. K. 1991. Inflammatory bowel disease. *New Engl. J. Med.* 325:928–937.

60. Crystal, R. G. 1997. Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985–1001.

61. Alvarez, R. D. and D. T. Curiel. 1997. A phase I study of recombinant adenovirus vector-mediated delivery of an anti-erbB-2 single chain (sFv) antibody gene from previously treated ovarian and extraovarian cancer patients. *Hum. Gene Ther.* 8:229–242.

62. Pastan et al. "A retrovirus carrying an MDR1 cDNA confers multidrug resistance and polarized expression of P-glycoprotein in MDCK cells." *Proc. Nat. Acad. Sci.* 85:4486 (1988)

63. Miller et al. "Redesign of retrovirus packaging cell lines to avoid recombination leading to helper virus production." *Mol. Cell Biol.* 6:2895 (1986)).

64. Mitani et al. "Transduction of human bone marrow by adenoviral vector." *Human Gene Therapy* 5:941–948 (1994)).

65. Goodman et al. "Recombinant adeno-associated virus-mediated gene transfer into hematopoietic progenitor cells." *Blood* 84:1492–1500 (1994))

66. Naidini et al. "In vivo gene delivery and stable transduction of nondividing cells by a lentiviral vector." *Science* 272:263–267 (1996))

67. Agrawal et al. "Cell-cycle kinetics and VSV-G pseudotyped retrovirus mediated gene transfer in blood-derived CD34+ cells." *Exp. HematoL* 24:738–747 (1996)).

68. Schwarzenberger et al. "Targeted gene transfer to human hematopoietic progenitor cell lines through the c-kit receptor." *Blood* 87:472–478 (1996)).

69. Fields, et al. (1990) Virology, Raven Press, New York.

70. Martin, E. W. (ed.) Remington's Pharmaceutical Sciences, latest edition. Mack Publishing Co., Easton, Pa.

71. *Antisense RNA and DNA*, D. A. Melton, Ed., Cold Spring Harbor Laboratory, Cold Spring Harbor, N.Y. (1988).

72. Bacon T A, Wickstrom E. "Walking along human c-myc mRNA with antisense oligodeoxynucleotides: maximum efficacy at the 5' cap region." *Oncogene Res* 6(1):13–9 (1991).

73. Ho, S. P., Britton D H, Bao, Y., Scully M S. "RNA mapping: selection of potent oligonucleotide sequences for antisense experiments" *Methods Enzymol* 314:168–183 (2000).

What is claimed is:

1. A method of treating the inflammatory response of an inflammatory bowel disease in a subject, comprising intrarectally administering to the subject an amount of a STAT-4 antisense oligonucleotide comprising the nucleotide sequence of SEQ ID NO: 7 effective in treating the inflammatory response of the inflammatory bowel disease.

2. The method of claim 1, wherein the inflammatory bowel disease is Crohn's disease.

3. The method of claim 1, wherein the subject is human.

4. The method of claim 1, wherein the antisense oligonucleotide is administered as naked DNA.

5. The method of claim 1, wherein the antisense oligonucleotide is administered in a liposome.

6. The method of claim 1, wherein the antisense oligonucleotide is administered in a vector.

7. The method of claim 6, wherein the vector is a viral vector.

8. A composition comprising a STAT-4 antisense oligonucleotide consisting of the nucleotide sequence of SEQ ID NO: 7 in a pharmaceutically acceptable carrier.

9. The method of claim 6, wherein the vector is administered to a cell in the subject.

10. The method of claim 9, wherein the cell is in a transgenic animal.

* * * * *